(12) United States Patent
Dickert et al.

(10) Patent No.: US 6,223,589 B1
(45) Date of Patent: May 1, 2001

(54) OIL QUALITY SENSOR

(75) Inventors: Franz Dickert, Klosterneuburg; Peter Forth, Vienna; Peter Lieberzeit, Dornbirn, all of (AT); Günter Voigt, Gifhorn; Klaus Dieter Marquardt, Wolfsburg, both of (DE)

(73) Assignee: Volkswagen AG, Wolfsburg (DE)

( * ) Notice: Subject to any disclaimer, the term of this patent is extended or adjusted under 35 U.S.C. 154(b) by 0 days.

(21) Appl. No.: 09/299,126

(22) Filed: Apr. 26, 1999

Related U.S. Application Data

(63) Continuation of application No. PCT/EP97/05748, filed on Oct. 17, 1997.

(30) Foreign Application Priority Data

Oct. 26, 1996 (DE) ............................................. 196 44 572
Jul. 23, 1997 (DE) ............................................. 197 31 621

(51) Int. Cl.$^7$ ................................................. G01N 33/26
(52) U.S. Cl. ..................... 73/61.45; 73/61.41; 73/61.62; 73/53.01; 73/61.49; 310/311; 310/312
(58) Field of Search .................. 73/61.45, 581, 73/579, 53.01, 61.43, 61.44, 61.49, 61.41, 61.62, 54.41; 310/312, 313

(56) References Cited

U.S. PATENT DOCUMENTS

| | | |
|---|---|---|
| 4,741,200 | 5/1988 | Hammerle . |
| 5,151,110 | 9/1992 | Bein et al. . |
| 5,201,215 | 4/1993 | Granstaff et al. . |
| 5,306,644 * | 4/1994 | Myerholtz et al. .................. 73/61.49 |
| 5,341,128 * | 8/1994 | Keyser et al. ............................ 73/40 |
| 5,656,767 * | 8/1997 | Garvey, III et al. ................. 73/61.44 |
| 5,659,128 * | 8/1997 | Goldenberg .......................... 73/53.01 |
| 5,852,229 * | 12/1998 | Josse et al. .......................... 73/61.49 |

FOREIGN PATENT DOCUMENTS

| | | |
|---|---|---|
| 9614573 | 5/1996 | (DE) . |
| 59-126931 | 7/1984 | (JP) . |
| 7174685 | 7/1995 | (JP) . |

OTHER PUBLICATIONS

Wulff, Guenter. Angew. Chem. Int. Ed. Engl. (1995), 34 (17), pp. 1812–1832.*

Mosbach, Klaus. Trends Biochem. Sci. (1994), 19(1), pp. 9–14.*

* cited by examiner

Primary Examiner—Hezron Williams
Assistant Examiner—Michael Cygan
(74) Attorney, Agent, or Firm—Baker Botts L.L.P.

(57) ABSTRACT

The chemical and/or physico-chemical determination of the ageing of a motor oil is very expensive and requires measuring methods which cannot be carried out on board a motor vehicle. The determination of only one oil condition parameter, for example the viscosity, only enables conditional statements to be made with respect to oil quality since conflicting effects may exist to varying degrees in this case. According to the invention, oil quality can be determined by a quartz base coated with a sensitive layer. The sensitive layer has a surface or volume which is adapted to an oil component and is suitable for the repeated incorporation and release of the oil component according to the concentration thereof. When the oil component is present, it is incorporated in the sensitive layer causing the resonant frequency of the layer to decrease via a mass effect or causing an effective increase of the component thickness or mass. As the oil ages, the proportion of the component incorporated in the sensitive layer decreases, so that the resonant frequency increases. A non-sensitive layer is used as a reference by which the viscosity effect of the oil on the oscillation of the quartz and the variation in viscosity of the motor oil are determined as a second important oil quality parameter.

13 Claims, 8 Drawing Sheets

OIL QUALITY SENSOR

This is a continuation of copending International application No. PCT/EP97/05748 filed Oct. 17, 1997.

BACKGROUND OF THE INVENTION

The present invention relates to an oil quality sensor, to a process for oil quality determination, and to the use of a sensor.

In the course of time motor oils have developed into high-tech products, which are one of the prerequisites for ensuring high engine performances. In this connection the term "motor oils" is a collective designation for basic oil components made of mineral oil, hydrocracking agents and synthetic components. Motor oils also contain an additive which is added in the form of a ready-made mixture ("packet"), as well as viscosity improvers (VI). Motor oils serve as lubricants for the engines as well as cooling and sealing media. Furthermore, they are intended to clean and keep clean all engine parts. The VI improvers ensure a more favorable viscosity temperature behavior than is shown by the pure basic oils. Depending on the requirements, the proportion of additives and VI improvers added to the oil usually ranges between 5 and 25%.

Further tasks of the additives in motor oils are: improvement of the corrosion-protection properties of the oils and reduction of sludge deposits and oil thickenings, as well as abrasion protection at frictional partners under all occurring loads. The thermal stresses on motor oils are high: in the sump they average about 100 to 150° C., and in the region of the upper piston ring zone, temperature peaks of between 200 and 350° C. may occur.

During their use the oils age, and primarily it is the additive components and VI improvers that are decomposed (used up). Unused, partially oxidized and polymerized fuel components are responsible for a considerable part of oil aging. Thus, the aging of oil is brought about by the effect of temperature and reactive combustion products (radicals) as well as by exceeding the dispersibility of the oils for solids and products of aging. As a result, the properties of the oil necessary for trouble-free operation of the engines are drastically worsened. An increased viscosity has the effect, e.g. at start-up, of causing a more prolonged transport of the oil to the places to be lubricated, resulting in increased abrasion.

The consumption of dispersion additives results in worsening of the ability of the oils to keep the engines clean, particularly at critical lubrication points such as the region of piston rings/slots and top lands, and in worsening of the prevention of deposit formation at valves and in valve drive.

Hence it is desirable to continuously or at brief intervals determine the deterioration of the properties of mineral oils which necessarily occur during engine operation, i.e. to determine it e.g. one or more times during the operation of a combustion engine.

However, until now reliable sensors for oil condition analysis have not been successfully developed, so that for prolonged operation of a motor oil in the engine, particularly in nonstationary engines, it is necessary to carry out an on-board analysis, i.e. an analysis done directly on the engine.

So far various oil sensors have been developed which measure the viscosity, TAN (total acid number) or fill level, in particular. Here a special difficulty is due to the use of different oils in the same combustion engine, as well as the compensation for different aging effects on the measured property. For example, it is known from U.S. Pat. Nos. 4,675,662 and 4,721,874, EP No. 527,176 B and JPN. Appl. Phys. 1993, Acoustic Plate Viscosity Sensor, to utilize the aging-related change in viscosity of the oil as a parameter for the oil condition. This is done via acoustic transit-time changes, phase shift or via resonance frequency changes of a quartz oscillator. Here, problems are presented by the frequent lack of a possibility to perform the measurement on board, on the one hand, and by the possible counteracting effects of "decomposition of the motor oil and dilution by fuel" on the other hand, an effect which reduces viscosity, as opposed to the "linkage of decomposition products." which increases viscosity, as long as these products do not separate out as sludge.

Because of their basic principle, neither TAN or TBN (total basic number) is suitable for an on-board measurement, inasmuch, in these methods, old oil is titrated with KOH. More recent set-ups, e.g. those known from SAE 910497, SAE 962112, U.S. Pat. Nos. 4,675,662, 4,792,791 and 5,200,027 show interesting solutions which, operate e.g., with capacity sensors, measurement of ionic migration or a potential difference, with electrochemical solid cells or with corrosion sensors. Some of these set-ups are inexact, still too large and too heavy, or require a sacrificial structural component which is basically undesirable. Also, mathematical models (SAE 870403) and HC-waste gas sensors (DE 42 35 225) are known which so far did not lead to a breakthrough. Nor are fill level sensors very suitable, since they fail when e.g. the engine oil is greatly diluted by fuels.

In "Molecular Imprinting of Chemically Sensitive Coatings—New Strategies in Sensor Designs and Fabrication" by F. L. Dickert, P. Forth, P. Lieberzeit, M/ Tortschanoff, W.-E. Buist, U. Knauer and G. Fischerauer in "Sensor 97", 8. International Fair, Nuremberg, 1997, molecular imprinting for mass-sensitive sensors in gases and liquids is described in detail.

SUMMARY OF THE INVENTION

The object of the present invention is to provide a sensor that can undertake measurements on board a combustion engine, said sensor being designed for determining the aging of an oil in a highly reliable and trouble-free manner.

When, in the following part of the specification reference is made to a layer, surface, volume or material, said reference logically applies to the whole group as well as to all uses, processes and sensors or this invention. The term "layer" relates to a material firmly bonded to a substrate.

As a rule, the determination of the oil component to be analyzed is not only qualitative but, in particular, at least semi-quantitative. This means that the determination of nature of the analyte is accompanied by an accurate or estimated concentration and quantity determination of the analyte. In a qualitative determination, attainment of the determination threshold value, optionally in combination with a mathematic method (e.g. lapse of time), can be used for signaling (the oil change).

In accordance with the invention, the sensor can, in principle, be used in all liquids in which a material change of composition takes place, i.e. in which at least one component increases or decreases. Preferably, the sensor is used for characterization of a complex liquid, i.e. a liquid which contains components unknown as to structure and quantity, where, in particular, reproducibility of the exact composition of the liquid is, in most cases, no longer present, e.g. because the composition of the liquid is affected by a multiplicity of (undeterminable) influences. The sensor is used with particular advantage in an oil-containing liquid, and preferably in a liquid containing at least 30% and particularly 50% oil. In addition to the oil, other components may also be present, which optionally can also be recognized by the sensor. The sensor is preferably designed for one or more components of the oil which, during of the use of the oil (or the liquid) decrease in amount; however the sensor may also be designed for an increase of one or more components of the liquid. Such an increase takes place e.g. in the case of rising acidity which occurs with the aging of the oil, i.e. an increase of acidic compounds can also be determined. Advantageously, the sensor is designed for one or more main components of the liquid, i.e. such components which make up the main weight proportion of the liquid, e.g. of the oil composition.

The above-described acidic changes occurring upon the aging of a mineral oil are detectable by IR spectroscopy. Thus, compared with the new-oil IR spectrum, the old-oil IR spectrum in FIG. 8 shows distinct absorption bands of hydroxy groups at 3,353 $cm^{-1}$, which originate from alcohols or organic acids. Moreover, the old-oil spectrum contains an alcohol band at 1,159 $cm^{-1}$ (C—C—O skeleton vibrations for alcohols, particularly tertiary or secondary alcohols—but it could also be a P=O stretching vibration) and acid bands at 1,730 $cm^{-1}$ (C=O bands) and 1,277 and 1,241 $cm^{-1}$ (—C—O stretching vibrations) (Literature cited: The Handbook of Infrared and Raman Characteristic Frequencies of Organic Molecules—Daimay Lien-Vien et al., Academic Press. 1991). Particularly distinct are the acidic changes in the oil, detectable by IR spectroscopy via the intensive C=O bands of carboxylate or carboxy groups, as can be noted at 1,608/1,630/1,730/1,769 $cm^{-1}$.

In contrast to the sensors described in the introduction, the sensor used in the measurement according to the invention is one that can repeatedly incorporate and release at least one component of the liquid, advantageously in correspondence to the concentration of this component.

Compared with known sensors, such as e.g. glass electrodes, the sensor used according to the invention differs in at least one of the following features:

The component of the liquid has a molecular weight of $\geq 150$, particularly $\geq 200$;

The component of the liquid is significantly absorbed or adsorbed in the sensor;

The (determined) component of the liquid is not cationic, and especially not ionic;

It is not a boundary surface potential, electrochemical potential and/or hydrogen potential that is being determined as characteristic quantity.

The component is so chosen that in view of its affinity to the sensitive layer it changes during the use of the liquid; this is usually achieved by a concentration change of the substance in the liquid as a result of the latter's use.

According to the invention it is particularly advantageous to determine one (or more) components of the liquid in such a way that the component is incorporated in the sensitive layer or is evacuated therefrom, whereby a weight change of the sensitive layer takes place. The incorporation can be determined also as a volume effect, i.e. the incorporation of the analyte or analytes takes place essentially proportionally to the layer thickness, at least up to a certain layer thickness. By measuring the weight change a measure of the incorporation of the component(s) in question, and thereby a measure of its (their) concentration, are obtained. In addition or alternatively, the present invention ensures that one (or more) analytes (a component) in an oil and/or one (or more) oily analytes are determined through the incorporation of the analyte (or analytes) in the sensitive layer.

Suitable as analyte and/or oil is, in particular, a motor oil as used e.g. in internal combustion machines. Advantageously the analyte is at least one component of a new motor oil, but it may also be a component of the old oil, particularly an oxidation product, which forms during the use of the motor oil. Preferably, the analyte in this case again has an aliphatic residue, as is usually present in mineral or synthetic motor oils. Such hydrocarbon residues usually have a molecular weight of between 300 and 3,000. By the use, according to the invention, of the adapted sensitive layer it can be accomplished, e.g. that essentially either the new oil component alone incorporates in the layer, or essentially only the decomposition products do so (with keto, aldehyde and/or acid residues or their addition or condensation products).

It is particularly advantageous if the sensitive layer of the sensor is made up of a polymer. This permits a simple and inexpensive preparation and easy adaptation to an analyte. Suitable polymers are, in particular, polyurethanes and/or modified polyurethanes, e.g. those in which the OH component is at least partially exchanged against an $NH_2$ component. For detection of the decomposition products, particularly of acidic changes of the oil, it is advantageous if basic components are built into the polymer structure. This can take place, e.g. through the use of basic monomers or of prepolymers with basic residues, where the basicity is advantageously preserved during polymerization. Such a basic monomer is e.g. triethanolamine $N(CH_2CH_2OH)_3$, which acts as a cross-linking agent and whose tertiary amino group is preserved during polymerization to polyurethane. In such a polymerization the adaptation to old oil, i.e. polymerization, takes place in the presence of old oil which subsequently can again be dissolved out from the finished polymer. The nitrogen contained in the triethanolamine can then undergo polar interactions with the acidic components in the old oil, and thereby extract this component from a mixture, even in the presence of certain amounts of unused oil. In addition, the triethanolamine offers, in the layers obtained in this way, generally polar interaction centers for analyte molecules with adapted properties.

Advantageously, the adaptation to the analytes is generally accomplished by forming the layer together with the analyte, e.g. by mixing a mineral oil with the layer former, particularly with a monomer or prepolymer. The layer composition is preferably so chosen that the analyte, as also the whole liquid, is inert with respect to the layer, i.e. the latter does not decompose or is otherwise chemically changed.

Furthermore, according to the invention, the sensor is advantageously used together with a nonsensitive sensor (measurement component of the same structure as the sensor, but without the sensitive properties for a component of the liquid), which serves as reference. This permits a simple and safe measuring setup. Particularly advantageously, sensors of different sensitivity can be used together, in particular also in combination with a nonsensitive sensor. In that case one sensor is designed for the recognition of new oil, and the other sensor for the recognition of old oil. The sensors of different sensitivity can also serve mutually as reference, so that viscosity changes can be averaged out. As mentioned above, a third, nonsensitive sensor can be used with particular advantage, by means of which a change in viscosity is determined. It is possible with such combinations to recognize the most varied oil changes in a particularly reliable manner, so that the oil sensor can be used for the most varied oils (or other liquids). Moreover, by using several sensitive sensors (of different sensitivity) the failure of a sensor or a possibly reduced sensitivity of a sensor—as may occur with the use of the most varied oils—can be recognized, whereby a particularly high process reliability is assured.

The measurement itself is preferably carried out by inducing vibrations in the layer; e.g. a dielectric effect on the layer can be utilized as measurement principle. When the layer is made to vibrate the layer is advantageously coated on an oscillating crystal (quartz crystal), which is then excited to undergo vibrations. By loading the sensitive layer with the analyte the layer, corresponding to the loaded amount, becomes heavier, whereby the oscillation behavior is altered. From this it is again possible to draw conclusions regarding the amount loaded.

In addition to the reference by means of which the absolute viscosity (or a viscosity change) can be determined, it is advantageous to use a temperature sensor, since the viscosity is highly temperature-dependent (particularly in the case of motor oil).

Here, the temperature-dependent viscosity behavior of the liquid phase can be plotted e.g in a performance graph, through which the temperature correction of the measured value is carried out. Alternatively or additionally, the measurement can also be performed only at one or more specified temperatures.

As already mentioned, it is possible to use several sensors in parallel, sensors which are imprinted with different components of the liquid phase and/or with different liquid phases. In this way, different changes of the liquid phase can be recognized. This is of significance particularly in the use of the sensor in a motor oil, since here different oils with different components can be used, on the one hand, and, depending on the operating conditions of the engine, different aging processes can take place, on the other hand.

Belonging to the use of the sensor is also an electronic evaluation system, through which the sensor is operated on the one hand and by which the sensor signal is converted to the desired information. In the case of motor oil, the information can be in particular a message indicating that a change of motor oil is due.

In principle, it is possible in the present invention, to use practically any layer which contains a matrix with cavities and/or diffusion channels, and is compatible with (adapts to) a component of the liquid (analyte) to be determined, i.e. to incorporate the analyte according to its concentration (at a high concentration) or to evacuate it (at a low analyte concentration in the liquid).

The preparation of such adapted surfaces is known also as "molecular imprinting," and in the past such molecular-imprinted layers have essentially been used in gases only. Such molecular-imprinted layers can be prepared industrially and at a low cost. In generating the sensor layer, e.g. by a polymerization process, the analyte to be detected is added to the reaction mixture. During polymerization or hardening the analyte molecules leave their imprint in the matrix and can, after conclusion of the reaction, be evaporated or washed out from the (polymeric) network. For this purpose an analyte should be chosen which is inert with respect to the polymerization process and to the finished polymeric layer (or the reaction mixture should be suitably chosen). The quality of the molecular-imprinted layers depends on many effects, particularly on the choice of layer material (polymer), duration of polymerization, amount of solvent during layer preparation, temperature, amount of cross-linking agents, etc. As a result of this production process, there remain in the chemically sensitive layer analyte-adapted cavities and diffusion channels which are predestined for the reincorporation of the analyte. This imprinting leads, analogously to the lock and key principle, to analyte-specific interactions, corresponding to the analyte concentration. This imprinting process can be carried out not only with a chemically pure analyte but also with an analyte mixture of complex composition. In this manner it is possible, with the sensors produced, to characterize the manifold aging processes taking place in motor oils. Thus, according to the invention, a sensitive layer of this sort can be prepared e.g. by polymerization of a polyurethane with a specified amount of cross-linking molecules in the presence of e.g. fresh motor oil (e.g. for Otto engines; on mineral or synthetic oil basis). After rinsing out the oil from the polymerized oil there remain in the polymeric matrix the cavities adapted to the components of the fresh motor oil. By means of IR spectroscopy it can be shown that these cavities reincorporate new oil in a remarkably selective manner. The same applies also to imprinting with old oil, where during imprinting with old oil the selectivity is lower, i.e. small amounts of new oil are also incorporated, whereby the intensity of response (e.g. weight change, electronic signal) is also lower.

BRIEF DESCRIPTION OF THE DRAWINGS

Below, the invention is explained in greater detail by means of drawings and embodiments. Shown are in FIG. 1 IR spectra of Otto new oil and Otto old oil in carbon tetrachloride, $CH_2/CH_3$ stretching vibrations, FIG. 2 IR spectra of a non-imprint sample after various operating steps, $CH_2/CH_3/OH$ stretching vibrations.

EXPERIMENTAL

Preparation of Layers

Figure 1:
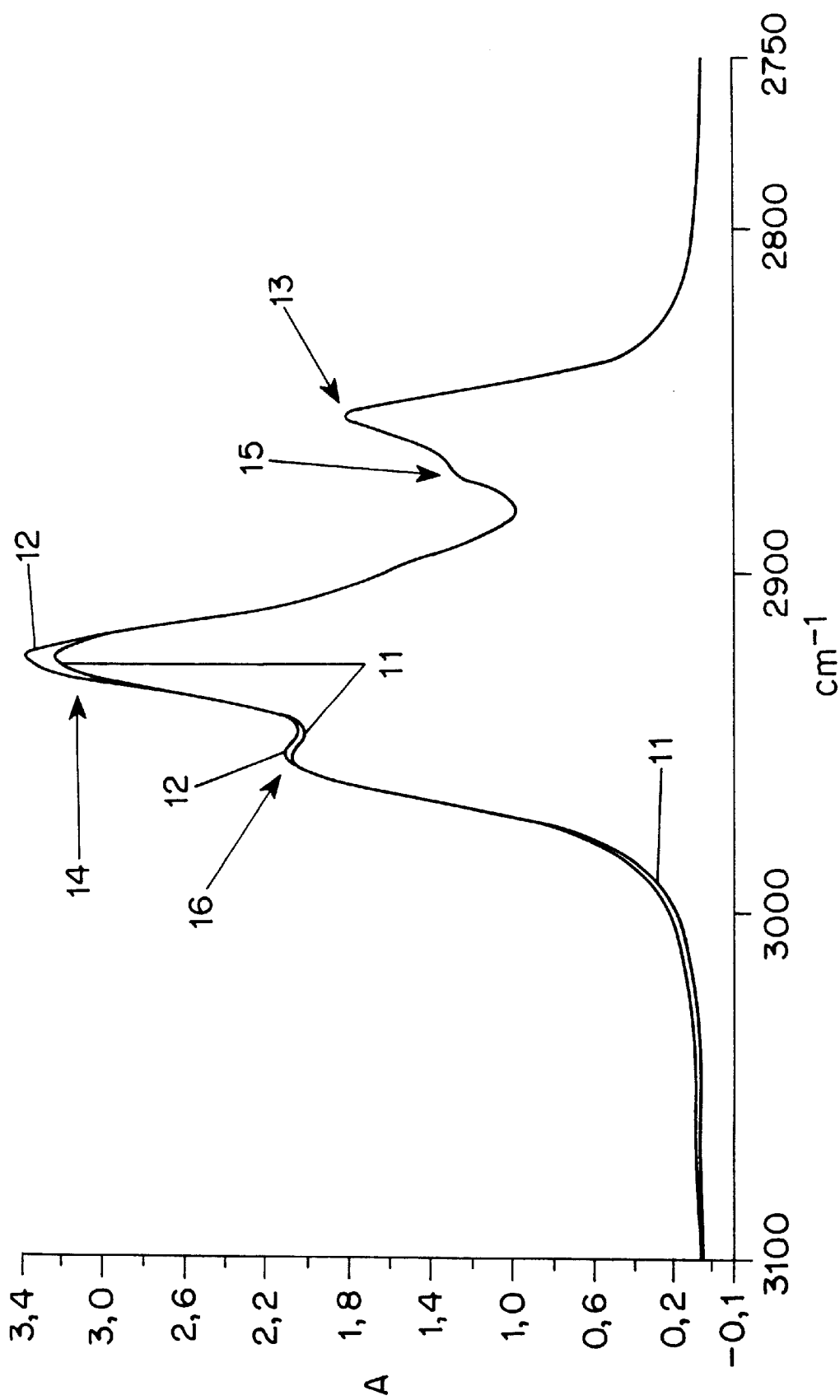

Sensor layers are prepared for determining the aging of motor oil. The chemically sensitive layers are produced by molecular imprinting of different polyurethanes. The following chemicals are used:

Phloroglucinol, highest purity

Bisphenol A, 97%

Triethanolamine, analytical grade

Diphenylmethane diisocyanate for synthesis (mixture of 70% diisocyanate and 30% triisocyanate)

Hexamethylene diisocyanate for synthesis

Tetrahydrofuran, dried, analytical grade.

Each of the synthesized polyurethanes contains, in stoichiometric ratio, one of the isocyanates and a mixture of both alcoholic components. The amount of phloroglucinol in the alcoholic component determines the degree of cross linking. A favorable degree of cross linking for imprints (for reincorporation of the analyte) is about 60% (generally 20 to 85%, depending on the polymer). When using hexamethylene diisocyanate a mixture of 60 mole-% phloroglucinol and 40 mole-% bisphenol A is used; for the isocyanate mixture the amount of phloroglucinol in the alcohol mixture is 40 mole-%, since in that case the isocyanate, too, can be a cross-linking agent due to its triisocyanate contents.

For preparation of the layers the individual components, together with the appropriate amount of new oil, are dissolved in THF. This mixture can be coated directly on small glass plates or small quartz plates for measurement by means of FT-IR, or it can be coated on oscillator crystals.

1) Hexamethylene Diisocyanate 0.76 mg (8 mmoles) of phloroglucinol, 91 mg (4 mmoles) of bisphenol A, 218 mg (13 mmoles) of hexamethylene diisocyanate and 116 mg of Otto new oil (corresponds to 30% of the mass of the monomer mixture and thus 23.1% of the total mass of the matrix) are dissolved in 1 mL of THF.

20 µL of this starting mixture is diluted with 180 µL of THF and 20 µL of the dilution is applied to the small glass plate or 2 µL on the QMB.

2) Diphenylmethane Diisocyanate 50 mg of phloroglucinol (4 mmoles), 137 mg of bisphenol A (6 mmoles), 274 mg of diphenylmethane diisocyanate (10.4 mmoles) together with 138 mg of oil are dissolved in 1 mL of THF. Dilution and application analogously to the preceding layer.

3) Triethanolamine

Of the individual components, solutions having a concentration of 2.5 mmoles per 2 mL of dried THF are prepared, meaning that the following amounts are weighed out:

Diphenylmethane diisocyanate 657 mg

Phloroplucinol 315 mg

Bisphenol A 570 mg

Triethanolamine 373 mg

Otto old oil was weighed into Eppendorf flasks (62.8 mg when the oil content in the layer is 30%, 48.9 mg for 25%, and 36.7 mg for 20%) and dissolved in 0.5 mL of THF.

To this solution were first added the alcoholic components with the aid of a glass pipet, and the isocyanate only shortly before the application of the isocyanate. The composition of the mixtures was as follows:

Bisphenol A 148 µL solution

Trifinctional alcohol 100 µL solution

Isocyanate 231 µL solution

The two trifinctional components phloroglucinol and triethanolamine are mixed in the required proportion (e.g. 10% TEA in the layer→10 µL of TEA solution and 90 µL of phloroglucinol solution).

The best old oil reincorporations were found with 10% and 20% TEA.

FT-IR Measurements

The small plates polymerized during the night are measured in a FT-IR device (Perkin-Elmer FTIR 2000) against an small empty quartz plate as blank. For an interpretation, the symmetrical and the antisymmetrical methylene vibration at 2,856 $cm^{-1}$ and 2,921 $cm^{-1}$, respectively, are made use of.

The essential measuring points are obtained according the following operational steps.

1.) Polymerization.

2.) Extraction of the motor oil from the layer by stirring in n-heptane.

3.) Reincorporation of new oil (placement in oil for 1 night, stirring). To remove the superficial oil, the small plate is first wiped dry with paper, and then rinsed out with about 1 mL of n-heptane.

4.) Renewed extraction of the oil and placement in old oil (analogously to 2, 3).

Mass-Sensitive Measurements

The reaction mixture is coated on the quartz oscillator. To achieve a constant layer thickness over the entire circular electrode region, the so-called spin-coating method is used, in which the sensor is rotated at 200–400 rpm (depending on the viscosity of the layer material) during polymerization. The layer thickness is about 1.5 µm, which generates a frequency shift of about 75 kHz. The mass-sensitive measurement is carried out with a network catalyst, whereby a high frequency of variable frequency is applied to the coated quartz component and in this way the damping behavior of the component is determined. This takes place in the resonance region of the transverse shear vibration of the quartz. The frequency of the smallest damping is then read from the computer and represented as a function of time. At the beginning of the measurement the sensor is immersed in thermostated new oil (T=50±0.1° C.). For a faster adjustment of the sensor effect the oil samples are thoroughly mixed by means of a dip stirrer at about 700 rpm. Then, after achieving constancy of the sensor signal the measured oil is changed. The old oil used is likewise pre-thermostated. The frequency of the smallest damping (resonance frequency) then changes on account of two opposite effects. First, the viscosity increase (in the case of viscous old oil) induces a frequency lowering, which—in the case of chemically sensitive coating—is partly compensated by a mass effect. The latter is brought about by the outward diffusion of molecules which have previously been imbedded in the layers. In uncoated and nonsensitively coated quartz the viscosity effect amounts to 18,000 Hz, and in the sensitively coated components the frequency shift varies, according to the polymer layer, between 11,000 and 16,000 Hz. Thus, depending on the layer used, the mass effect amounts to 1,000 to 5,000 Hz.

As can be seen from FIG. 1, in the aliphatic region of interest the IR spectra of fresh (11) and used (12) Otto motor oil show virtually no difference. The intensities of the symmetrical (13) and asymmetrical (14) methylene vibrations are nearly identical, and in the region of the methyl vibrations, too (symmetrical 15, asymmetrical 16) there are virtually no recognizable differences.

Figure 2:
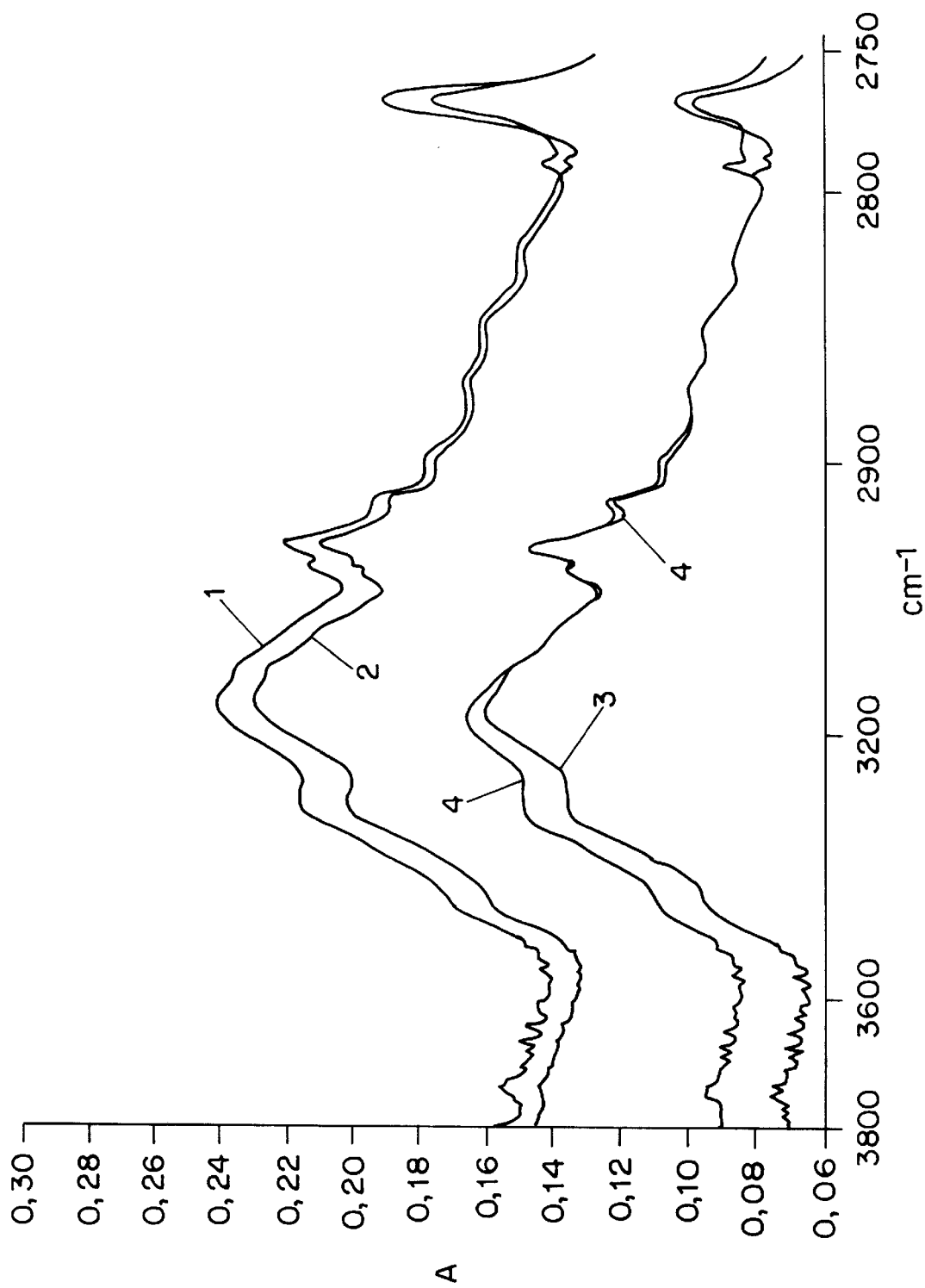
Figure 3:
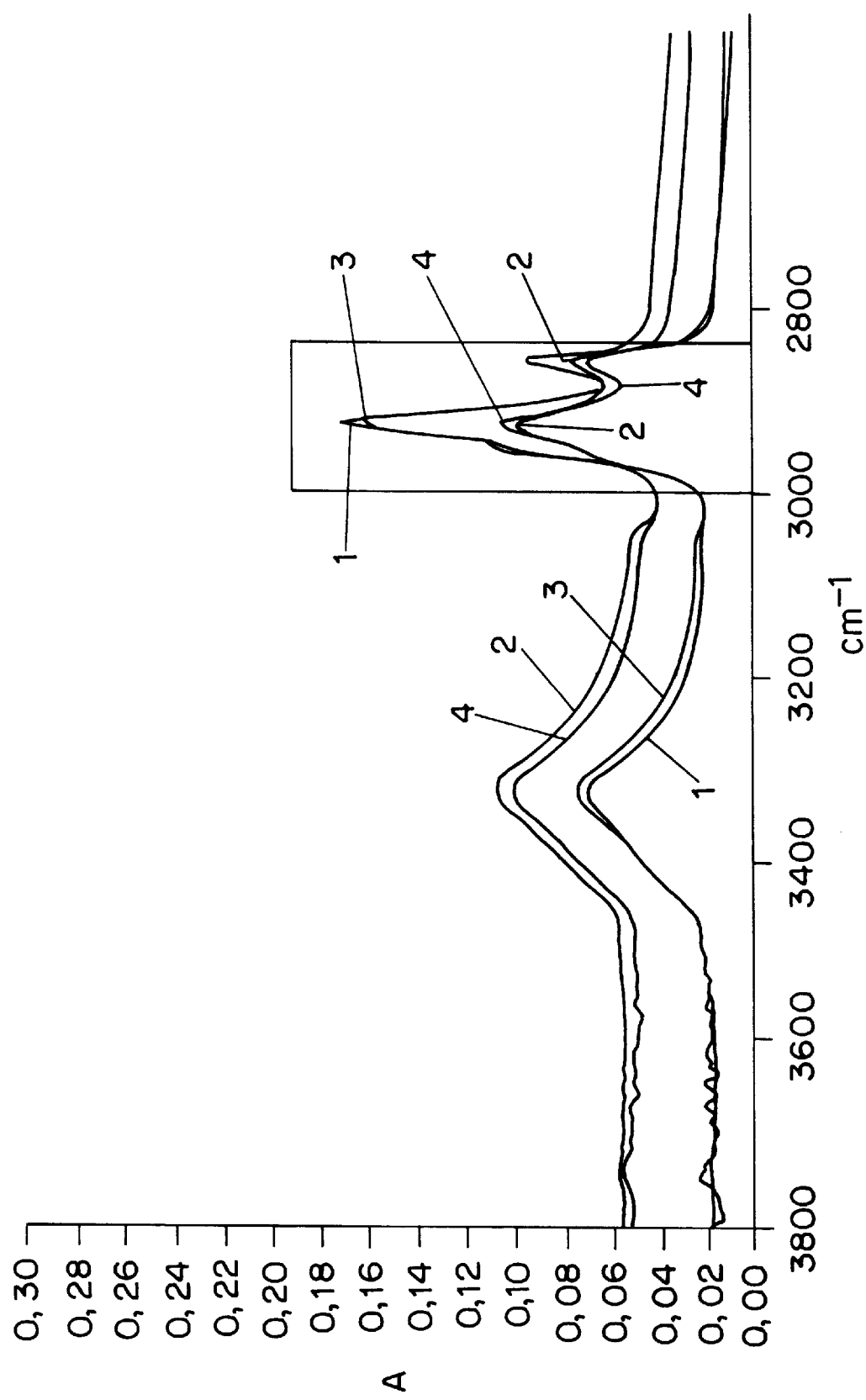
FIG. 3 IR spectra of an imprint sample after the individual operating steps.
Figure 4:
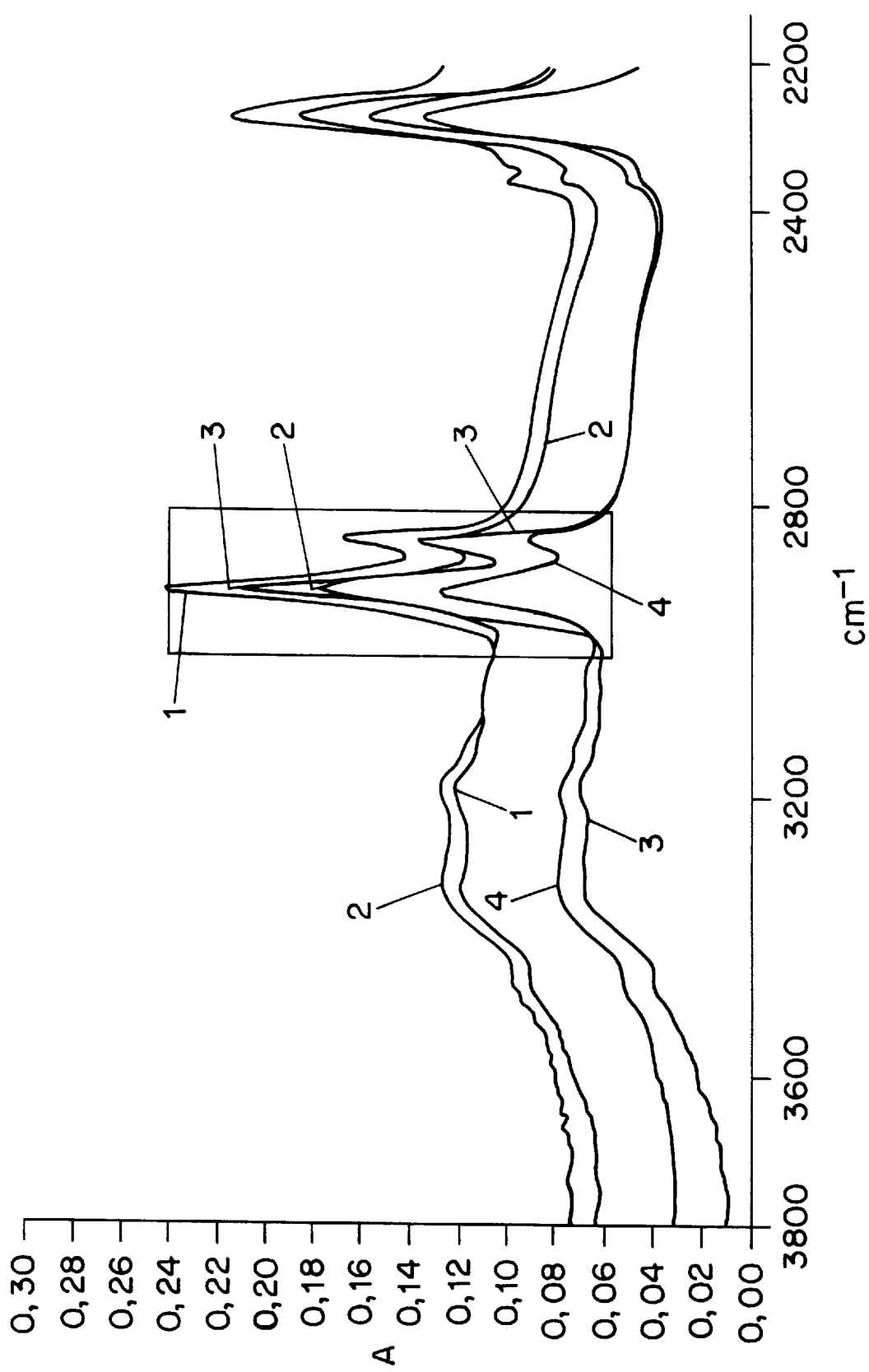
FIG. 4 IR spectra of an imprint sample of an amine-containing polymer after different operating steps.

FIGS. 2 to 4 show the IR spectra of three polymers recorded after the individual operational steps, respectively. A polymer prepared without imprinting (FIG. 2) is compared with a from identical material imprinted with fresh oil (FIG. 3) and an amine polymer imprinted with fresh oil (FIG. 4). The IR spectra were recorded after the following process steps:

1. Curing the polymer (in FIGS. 3 and 4 incl. an Otto new oil);
2. Rinsing out the mobile portion of the imprint used for imprinting (Otto new oil) with nheptane;
3. Twelf hour storage of the polymer in Otto new oil with subsequent rinsing out the surface layers,
4. Twelf hour storage in Otto old oil with subsequent rinsing out the surface layers.

In the samples with imprinted sensor layers (FIGS. 3 and 4) the intensities of the aliphatic peaks (about 2,900 $cm^{-1}$, underlaid) decrease after the imprint is rinsed off, thus, a major part of the oil can be removed from the polymeric matrix. Through storage in new oil the intensities again increase approximately to the baseline value, thus the new oil again incorporates in the polymer matrix (the same spectra are obtained on repeated imbedding and evacuation of the new oil). The spectra further show that old oil (4) is not imbedded in the polymer framework, the IR spectrum corresponds to that of the sample rinsed out with n-heptane.

In the samples without imprint (FIG. 2) only slight intensity changes are obtained during operational steps 1 to 4, so that it may be excluded that, in the case of the imprinted samples, a pure superficial adsorption takes place. The slight effects in this case point to a slight porosity of the non-imprint samples near the surface. Here the polymer is a pure polyurethane layer. The relevant signal is at about 2,900 wave numbers (the broad bands at about 3,200 $cm^{-1}$ mainly represent vibrations of acidic hydrogen). The same material behaves very differently when polymerized with fresh oil (FIG. 3). One clearly sees the intensity loss of the aliphatic CH vibrations after rinsing the layers with n-heptane (1→2), which is attributable to the rinsing out of the oil added during polymerization. If the rinsed layer is placed in new oil overnight, the signal again attains nearly its baseline value (2→3.), thus the new oil is again incorporated. Renewed rinsing and placement in old oil results in the same signal intensity as with the rinsed layer (2.→4.), i.e. in contrast to new oil, the old oil was not incorporated in the layer.

Figure 5:
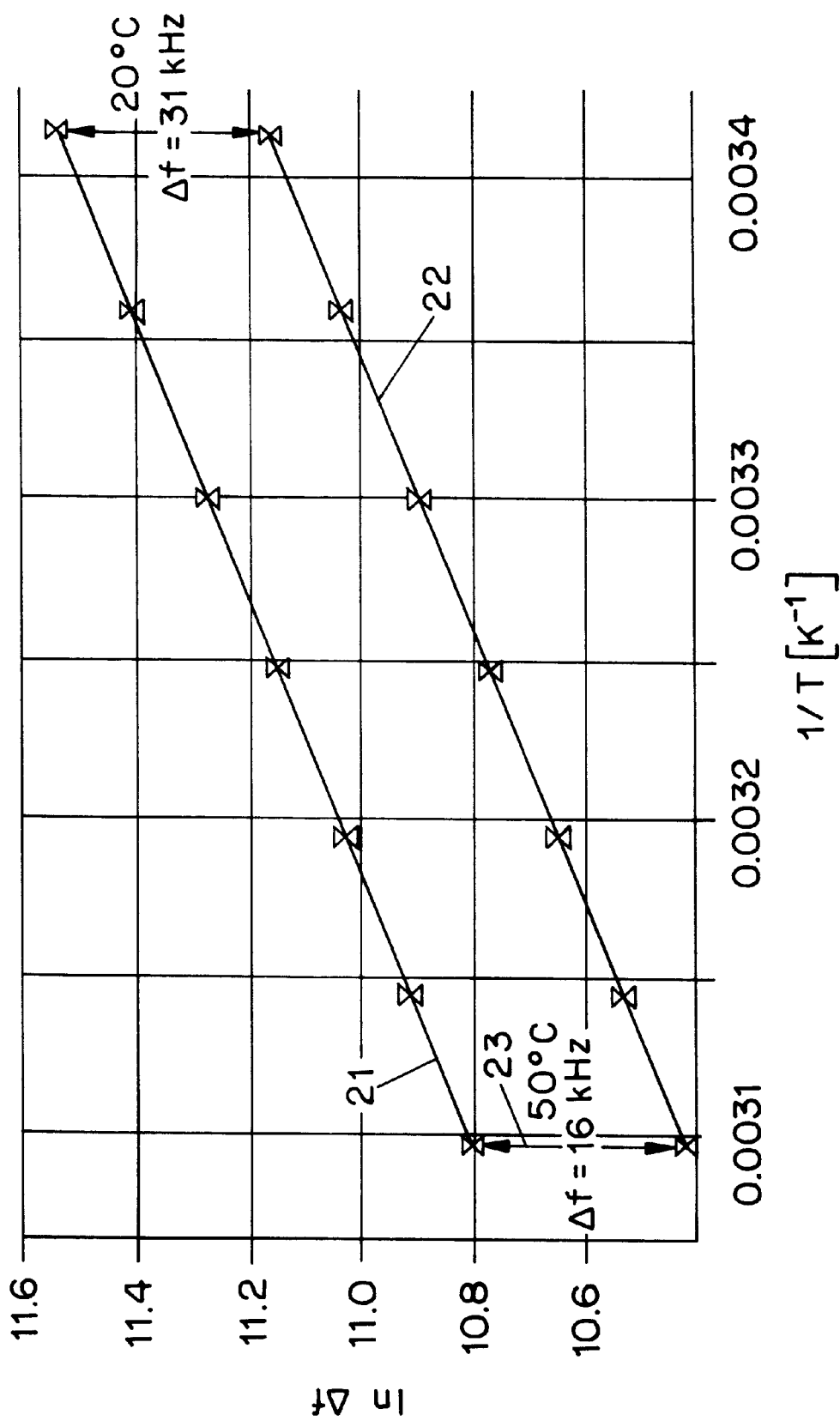
FIG. 5 Temperature dependence of the frequency response of an uncoated quartz microbalance (QMB) in old and new oil.

FIG. 5 shows the temperature dependence of the resonance frequency of an uncoated QMB in old oil 22 and new oil 21, respectively. At 50° C. the frequency shift 23 of the quartz immersed in the respective oil amounts to 16 kHz on transition from new oil to old oil. Similar values are obtained in quartzes that are coated with polymers which cannot incorporate any oil (unimprinted polymer, non-imprint sample). A linear relationship can be observed between the logarithm of the frequency shift and the reciprocal absolute temperature. Quartz oscillators with nonsensitive polymer layers (non-imprint) give straight lines displaced in parallel, whose slopes differ by a maximum of 10%. From this it follows that the measured frequency shifts are pure viscosity effects and not mass effects.

Figure 6:
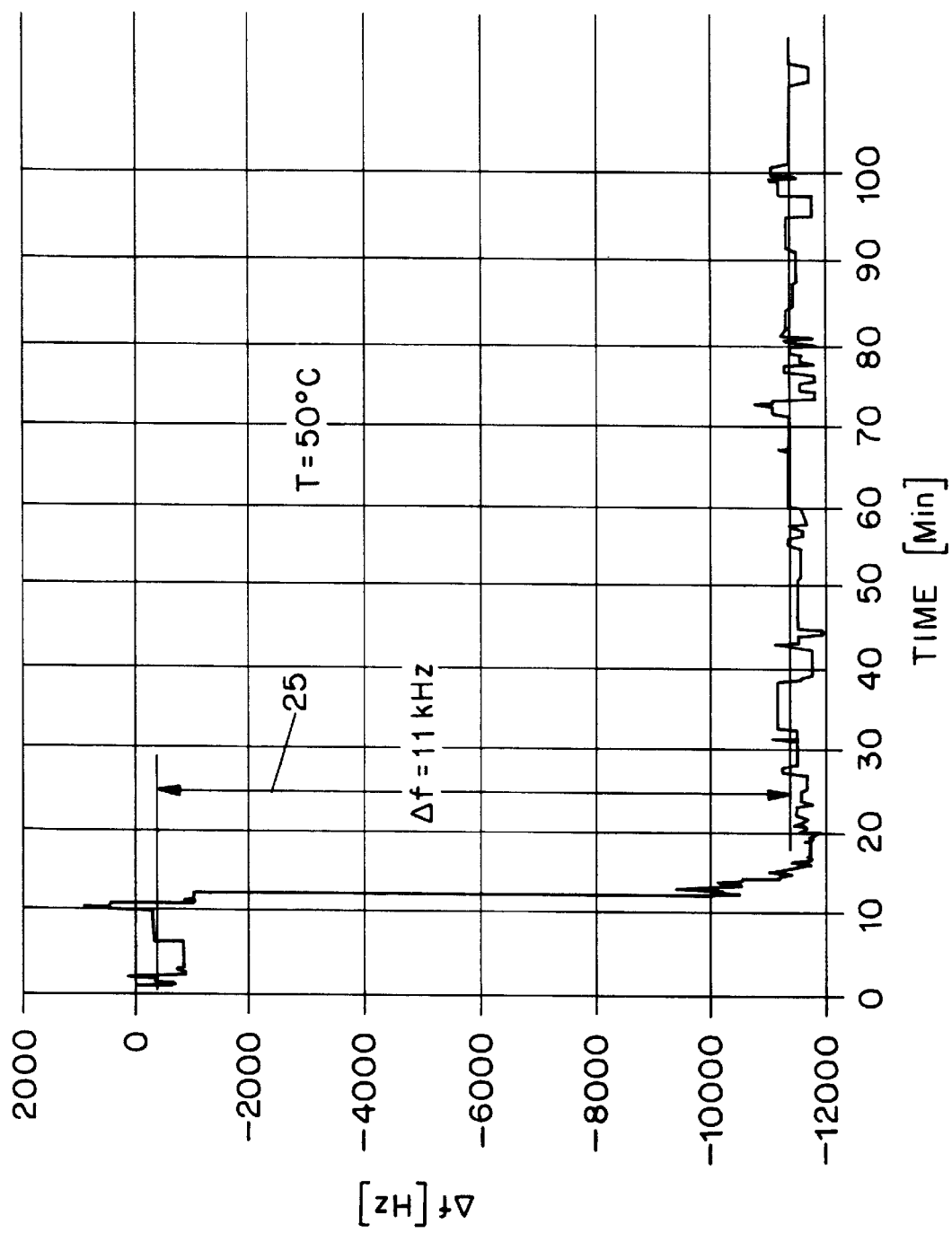
FIG. 6 Frequency response of a QMB imprinted with new oil when changing from new oil to old oil.
Figure 7:
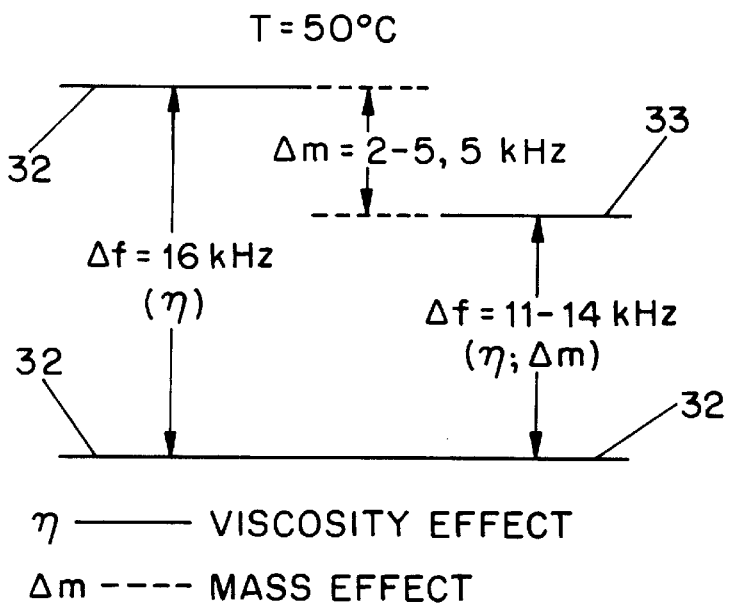
FIG. 7 Comparison of the frequency responses of mass-sensitively and non-masssensitively coated QMB.

The frequency shift, which can be observed upon the transfer of a QMB (quartz micro balance) loaded with a sensitive layer (imprint sample) prepared by molecular imprinting from new oil to old oil is, at a temperature of 50° C. initially by 2 to 3 kHz lower than for a non-imprint quartz. Depending on the polymer layer the frequency shift can be even smaller, FIG. 6 shows a frequency shift 25 of 11 kHz for a quartz with a sensitive layer, i.e. this frequency shift 25 is by 5.0 kHz below the that of an uncoated quartz (even a quartz with a non-imprint layer can be used here). This difference in frequency response of a sensitively coated QMB relative to all other quartzes results from a reversible incorporation of Otto new oil in the layer and evacuation of Otto new oil from the layer when it is dipped into old oil. The frequency shift for different non-sensitive layers is approximately the same. This state of affairs is represented in FIG. 7 in greater detail.

The quartz not provided with a sensitive layer reacts almost exclusively to the different viscosity of new oil 31 and old oil 32, without consideration of their chemical compositions. The frequency response Δf is 16 kHz. In the measurement, carried out in parallel, of the frequency shift on the quartz provided with a sensitive layer (see above) yields an amount of only 11 to 14 kHz (depending on the sensitive layer) is obtained, i.e. about 2 to 5 kHz less. This amount results from the mass effect, i.e. from the weight difference between the sensitive layer loaded with the new oil 33 and the evacuation of the new oil 33 from the sensitive layer, when it is stored in old oil 32.

With the use of a quartz with non-sensitive layer (or without coating) as reference the viscosity change of new oil to old oil and the consumption of new oil (aging) can be determined. The latter varies proportionately with the mass effect Δm. Thus, according to the invention, the sensor permits continuous monitoring of the aging of a motor oil by determining the increase of the mass effect, while the change in viscosity, which goes from an increase toward a decrease, is taken into account by the reference.

Figure 9:
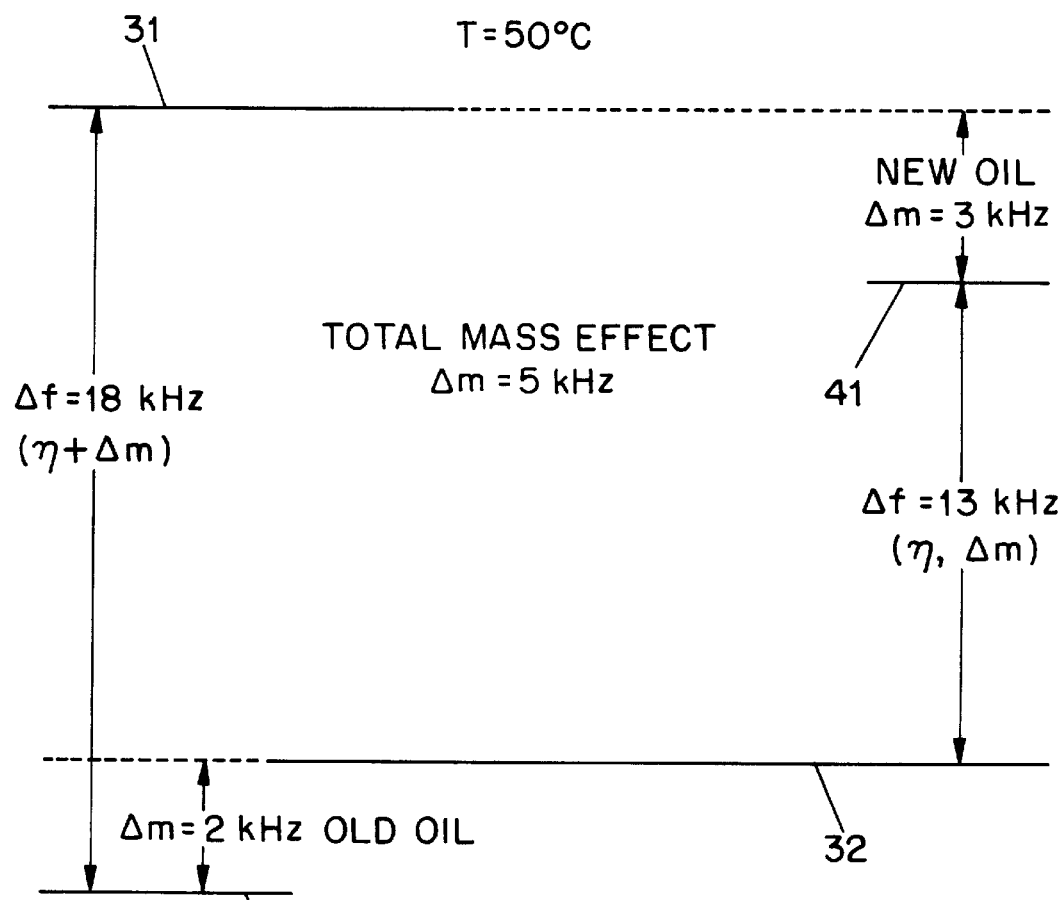
FIG. 9 Comparison of the frequency responses of QMB imprinted with new and old oil.
Figure 8:
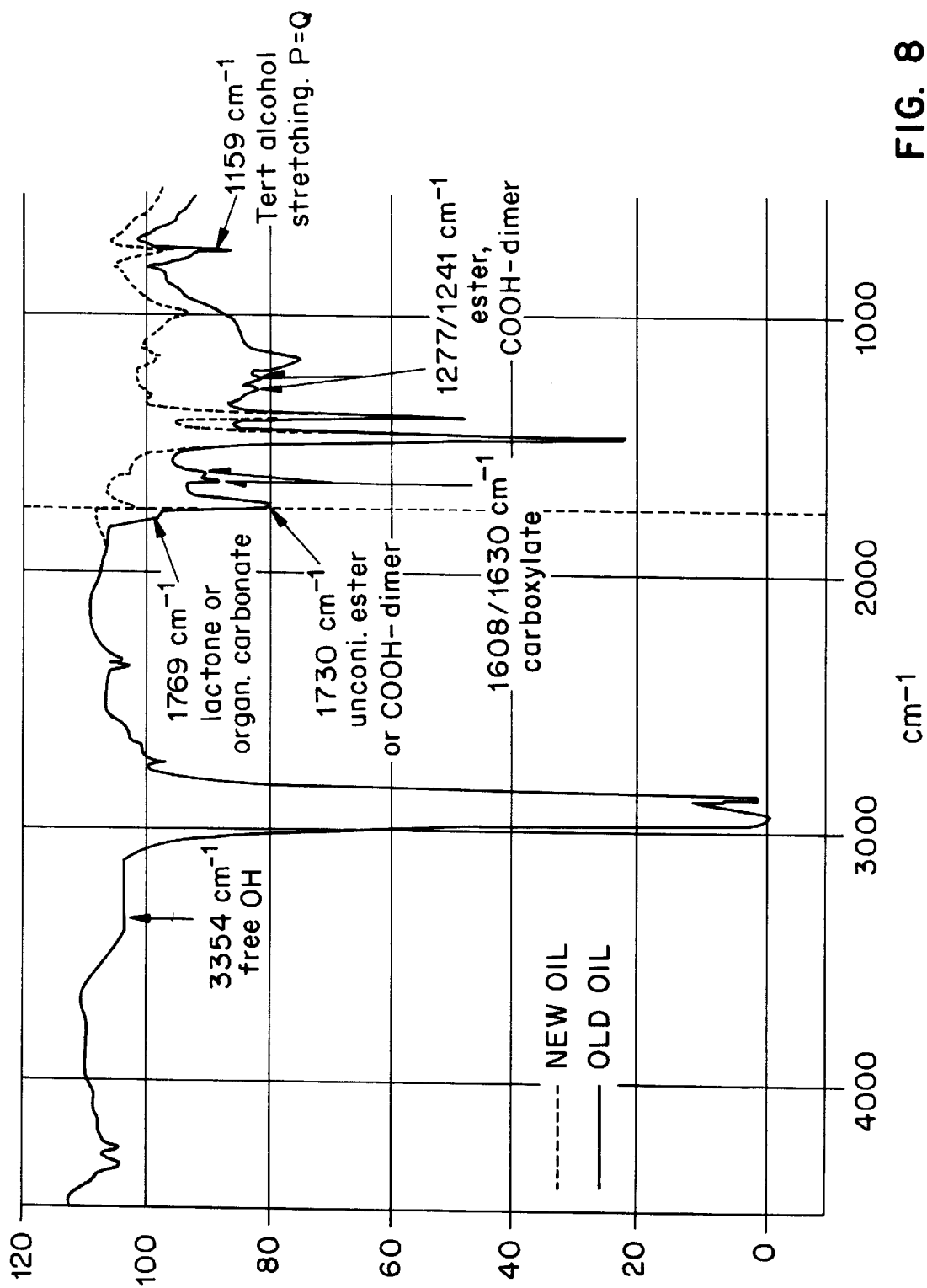
FIG. 8 IR spectra of fresh and used Otto motor oil.

Alternatively or in addition to the quartz sensitive to or insensitive to new oil, it is possible to use also a quartz sensitive to old oil. FIG. 9 shows a comparison between a quartz coating 42 imprinted with old oil and a quartz coating 41 imprinted with new oil. The quartz imprinted for new oil shows, in the new oil, a frequency shift of 18 kHz, which decreases in old oil to 13 kHz. By contrast, the quartz 42 imprinted for old oil in fresh oil shows a frequency shift of 16 kHz, which increases in old oil to 18 kHz.

By using triethanolamine, it is assumed that hydrogen bridge formations can also be used for binding the acidic component of old oil. The utilization of these polar interactions offers the potential for the development of a sensor for any motor oil, since as a result of combustion processes carboxyl groups (acid groups) are always formed. By means of polymer building blocks it is possible to obtain interactions adapted to the individual acidic components of old oil. The old-oil sensor can be designed also as threshold value sensor, which responds at a preset acidity and thereby signals an oil change. With the acidity it is possible to detect a property of the oil which is independent of the brand and quality of the oils, so that even synthetic oils can be monitored with respect to their aging.

Thus, in accordance with the invention, oil quality determination is advantageously carried out by means of a quartz coated with a sensitive layer. The sensitive layer has a surface adapted to at least one oil component, which, corresponding to the concentration of the oil component is predestined for repeated incorporation and evacuation of the oil component. In the presence of the oil component the latter is stored in the sensitive layer, whereby, via a mass effect—an effective increase of the thickness or mass of the structural part—the resonance frequency decreases. As a result of aging of the oil the component which has been incorporated in the sensitive layer decreases, whereby the resonance frequency increases. Used as reference is a non-sensitive layer, through which that of the effect of oil viscosity on the vibration of the quartz is determined.

What is claimed is:

1. A process for determining the content of an analyte which is a selected motor oil constituent in a motor oil comprising:

providing a sensor having a sensitive layer with at least one of a surface especially adapted to releasably absorb or adsorb at least one specific analyte which is a motor oil constituent and a layer volume especially adapted to releasably absorb or adsorb at least one specific analyte which is a motor oil constituent, which surface or layer volume is arranged for repeated analyte-specific incorporation or release of the analyte;

bringing a motor oil containing the analyte into contact with the sensitive layer; and determining a weight change of the sensitive layer according to an existing affinity of the analyte to the layer, wherein the sensor is arranged for determining ageing of a motor oil.

2. A process according to claim 1 wherein the sensitive layer is a polymer.

3. A process for determining the content of an analyte which is a selected motor oil constituent in a liquid phase comprising providing a molecular-imprinted material and determining the content of an analyte corresponding to the molecular imprint in the motor oil by determining a weight change of the material wherein the content of the analyte is used to determine ageing of a motor oil.

4. A process according to claim 3 wherein the molecular-imprinted material is contained in a sensor.

5. A process according to claim 3 wherein the molecular-imprinted material has at least one of a surface adapted to at least one analyte and a layer volume adapted to at least one analyte, and the surface or layer volume is arranged, according to an existing affinity of the analyte to the molecular-imprinted layer, for repeated analyte-specific incorporation and release of the analyte.

6. A process according to claim 3 wherein the molecular imprinted material is a polymer.

7. A process according to one of claims 6 and 2 wherein the polymer is selected from the group consisting of a cross-linked polyurethane and a derivatized polyurethane.

8. A process according to claim 6 or 2 wherein the polymer contains basic groups.

9. A process according to claim 6 or 2 wherein the polymer contains amino groups.

10. A process according to claim 6 or 2 wherein the polymer is formed in the presence of used motor oil or is imprinted with used motor oil.

11. A process for determining the content of an analyte which is a selected motor oil constituent in a motor oil comprising providing a sensor having a sensitive layer with at least one of a surface adapted to releasably absorb or adsorb at least one specific analyte and a layer volume adapted to releasably absorb or adsorb at least one specific analyte which is a motor oil constituent, and in which the surface or volume is arranged, according to an existing affinity of the analyte to the layer, for repeated analyte-specific incorporation or release of the analyte, and bringing the sensitive layer into contact with an analyte, wherein the sensor is arranged for determining ageing of a motor oil.

12. A process according to claim 11 wherein the analyte is a constituent of a motor oil for a combustion engine.

13. A process according to claim 12 wherein the analyte is a constituent of a motor oil group consisting of a fresh motor oil and a used motor oil.

* * * * *